US010016521B2

(12) United States Patent
Hsu (10) Patent No.: US 10,016,521 B2
(45) Date of Patent: Jul. 10, 2018

(54) SPECT RADIONUCLIDE-LABELED TRIMERIC CYCLE RGD PEPTIDE, PREPARATION METHOD THEREOF AND IMAGING METHOD THEREOF

(71) Applicant: Bailing Cloud Biomedical Technologies Innovation, Taipei (TW)

(72) Inventor: Bailing Hsu, Taipei (TW)

(73) Assignee: Bailing Cloud Biomedical Technologies Innovation, Taipei (TW)

( * ) Notice: Subject to any disclaimer, the term of this patent is extended or adjusted under 35 U.S.C. 154(b) by 329 days.

(21) Appl. No.: 15/002,690

(22) Filed: Jan. 21, 2016

(65) Prior Publication Data
US 2016/0235871 A1 Aug. 18, 2016

(30) Foreign Application Priority Data

Feb. 12, 2015 (TW) .............................. 104104699 A
Jun. 22, 2015 (TW) .............................. 104120058 A (51) Int. Cl.
| | | |
|---|---|---|
| *A61K 51/00* | (2006.01) | |
| *A61M 36/14* | (2006.01) | |
| *A61K 51/08* | (2006.01) | |
| *A61K 51/06* | (2006.01) | |
| *C07K 1/13* | (2006.01) | |

(52) U.S. Cl.
CPC .......... *A61K 51/082* (2013.01); *A61K 51/065* (2013.01); *A61K 51/088* (2013.01); *C07K 1/13* (2013.01)

(58) Field of Classification Search
CPC ........ A61K 51/00; A61K 38/00; A61K 51/08; A61K 51/082; A61K 51/065; A61K 51/088; C07K 1/13
USPC .......... 424/1.11, 1.65, 0.69, 1.81, 1.85, 1.89, 424/9.1, 9.2, 9.3, 9.4, 9.5, 9.6; 514/1, 514/1.1, 13.3, 19.2, 19.3, 19.4, 19.5, 19.6, 514/19.7, 21.1, 21.9, 21.6; 530/300, 316, 530/317, 331, 333, 338, 328
See application file for complete search history.

(56) References Cited

U.S. PATENT DOCUMENTS 8,043,601 B2 * 10/2011 Kolb ................ A61K 47/48215
424/1.11

FOREIGN PATENT DOCUMENTS

CN 101428148 A 5/2009

OTHER PUBLICATIONS

Liu et al, Eur. J. Nucl. Med. Mol. Imaging, 2009, vol. 36, pp. 947-957.*

(Continued)

*Primary Examiner* — D L Jones
(74) *Attorney, Agent, or Firm* — Alan D. Kamrath; Kamrath IP Lawfirm, P.A.

(57) ABSTRACT

The disclosure is related to a chemical structure, a preparation and an imaging method of a tumor imaging tracer, especially to a SPECT radionuclide-labeled trimeric cyclic RGD peptide: $^{99m}$Tc-4P-RGD$_3$ which functions as a ligand to be combined with integrin $\alpha_v\beta_3$ receptor in tumor for tumor imaging. The preparation includes linking HYNIC-OSu with 4P-RGD$_3$ to form HYNIC-4P-RGD$_3$ and then chelating HYNIC with $^{99m}$Tc to create $^{99m}$Tc-4P-RGD$_3$ Animal biodistribution and imaging experiments reveal higher uptake in tumor and lower uptake in normal organs, therefore the disclosure can improve image quality, Through animal metabolic experiments, the original form of $^{99m}$Tc-4P-RGD$_3$ can be still excreted without the evidence of further metabolites in urine and feces. According to the disclosure, the tumor imaging tracer $^{99m}$Tc-4P-RGD; combined with the integrin $\alpha_v\beta_3$ solves the issue of high background uptake in normal organs, such that radio-labeled SPECT imaging tracers are more suitable for animal whole-body tumor evaluation.

5 Claims, 6 Drawing Sheets

(56) References Cited

OTHER PUBLICATIONS

Shi et al, Theranostic, 2011, vol. 1, pp. 322-340.*
Jiyun Shi et al., Evaluation of In-Labeled Cyclic RGD peptides: Effects of Peptide and Linker Multiplicity on Their Tumor Uptake, Excretion Kinetics and Metabolic Stability, Theranostics, Jul. 25, 2011, pp. 322-340, Ivyspring International Publisher, http://www.thno.org.
Peter A. Knetsch et al., [Ga]FSC-(RGD) a trimeric RGD peptide for imaging αvβ3 integrin expression based on a novel siderophore derived chelating scaffold—synthesis and evaluation, Nuclear Medicine and Biology, Oct. 6, 2014, pp. 115-122, 42 (2015), Elsevier Inc., http://dx.doi.org/10.1016/j.nucmedbio.2014.10.001.
Xiaoyuan Chen, Michael Tohme, Ryan Park, Yingping Hou, James R. Bading, and Peter S. Conti, Micro-PET Imaging of αvβ3-Integrin Expression with F-Labeled Dimeric RGD Peptide, Molecular Imaging, Apr. 2004, 9 pages, vol. 3—No. 2.
Zi-Bo Li, Weibo Cai, Qizhen Cao, Kai Chen, Zhanhong Wu, Lina He, and Xiaoyuan Chen, Cu-Labeled Tetrameric and Octameric RGD Peptides for Small-Animal PET of Tumor αvβ3 Integrin Expression, The Journel of Nuclear Medicine, Jul. 2007, 10 pages, vol. 48—No. 7, The Society of Nuclear Medicine, Inc.
Zi-Bo Li, Kai Chen, and Xiaoyuan Chen, Ga-labeled multimeric RGD peptides for microPET imaging of integrin αvβ3 expression, Eur J Nucl Med Mol Imaging, 2008, 9 pages, vol. 35, published online.
American Cancer Society, Cancer Facts & Figures 2015, Report, 2015, 56 pages, American Cancer Society, Inc., U.S.

* cited by examiner

SPECT RADIONUCLIDE-LABELED TRIMERIC CYCLE RGD PEPTIDE, PREPARATION METHOD THEREOF AND IMAGING METHOD THEREOF

CROSS-REFERENCE TO RELATED APPLICATIONS

This non-provisional application claims priority under 35 U.S.C. § 119(a) on Patent Application No(s). 104104699 filed in Taiwan, R.O.C. on Feb. 12, 2015 and Patent Application No(s). 104120058 filed in Taiwan, R.O.C. on Jun. 22, 2015, the entire contents of which are hereby incorporated by reference.

BACKGROUND OF THE INVENTION

Field of the Invention

The disclosure is related to a radioactive tumor imaging tracer and a preparation thereof in the field of single photon emission computed tomography (SPECT), and more particularly, to a SPECT radionuclide-labeled trimeric cyclic RGD (Arg-Gly-Asp) peptide: $^{99m}$Tc-4P-RGD$_3$, comprising a $^{99m}$Tc, four polyethylene glycol (PEG$_4$) and three trimeric cyclic RGD (Arg-Gly-Asp). The medicine can be expressed by integrin $\alpha_v\beta_3$ in the tumor after intravenous injection and can function as a ligand to be combined with integrin $\alpha_v\beta_3$ receptor in tumor for tumor imaging.

Description of Related Art

According to "Cancer Facts &. Figures 2015" published on American Cancer Society, in 2007-2011, the incidence rates for selected callers in U.S. are 535.8/100,00 for male and 419.1/100,00 for female. In 2015, the estimated number of new cases for selected cancers is 1,658,370. Therefore, it is important to develop cancer detecting medicines with lower cost and simpler preparation for diagnosis and prevention of cancer.

Currently, F-18 labeled fludeoxyglucose, $^{18}$F-FDG imaging agent is used for evaluating the glucose metabolism of tumor, such that the tumor can be diagnosed, which is beneficial for the detection and treatment of tumor However, the preparation of the F-18 labeled medicine is complicated and the cost is high, meanwhile, the treatment needs to involve expensive positron emission tomography (PET) or PET/Computed Tomography (PET/CT) for imaging. Thus, the diagnostic procedure is expensive and the use in clinical application cannot be widely performed. Especially, the diagnostic procedure cannot be performed in the hospitals without PET or PET/CT scanners, and the tumor examination of PET or PET/CT cannot be widely performed.

In current researches. PET radionuclide-labeled RGD (PET RGD) can be used in clinical researches. However, the yield of the preparation of the radioactive medicine is low (~40%), the quality control is complicated, such that the prepared medicine is even more expensive than $^{18}$F-FDG In addition, PET instruments are also needed for imaging, such that it is difficult to apply PET RGD for the clinical utilization.

As compared with $^{18}$F-FDG and PET RGD, SPECT labeled RGD cyclic peptide can be used for evaluating tumor, the preparation is simpler and can be imaged by SPECT or SPECT/CT, which are cheaper for tumor imaging, Thus, SPECT labeled RGD cyclic peptide has the advantages of lower cost and simple technique for future development. Especially, $^{99m}$Tc labeled cyclic peptide imaging can be used for evaluating the level of integrin $\alpha_v\beta_3$ in tumor, which is different from the $^{18}$F-FDG method. $^{99m}$Tc labeled cyclic peptide imaging can provide another important diagnostic value for malignant degree of tumor in diversity of tumor biological behavior.

Integrin $\alpha_v\beta_3$ is the integrin which has been studied the most. Integrin $\alpha_v\beta_3$ is expressed on the surface of multiple tumor cells and tumor neovasculars, such as glioma, lung tumor, thyroid tumor, hepatic tumor, teratoma and breast tumor. Integrin $\alpha_v\beta_3$ is not expressed or almost unexpressed in mature endothelial cells and most of the normal cells. The formation of neovasculars and lymphatics play an important role in tumor occurrence, development and migration. The formation of tumor neovasculars would enhance the tumor growing and migrating, and the formation of lymphatics is directly related to tumor migration. $\alpha_v\beta_3$ acceptors mediate the adhesion and migration of tumor cells and play an important role in the formation of tumor neovasculars and lymphatics migration. The expression level of $\alpha_v\beta_3$ is related to malignant phenotypes of malignant tumor, such as invasion and metastasis, and can be servers as an indicator of evaluating the malignant tumor in prognosis.

Integrin is a group of transmembrane glycoprotein, which is a heterodimer having a $\alpha$ sub unit and a $\beta$ sub unit combined by non-covalent bonds. It is also an acceptor of extracellular matrix proteins. It is specifically combined with receptor recognition sequence RGD of the extracellular matrix proteins (such as fibronectin, glass-binding protein, laminin, collagen and so forth). Integrin controls the formation of neovasculars and lymphatics. According to multiple researches, integrin controls proteolytic enzymes, such as matrix metalloproteinase, and integrin directly involves in degradation of extracellular matrix and enhances migration of tumor. The rich expression of integrin is the important molecule in enhancing migration and invasion of tumor cells and vascular endothelial cells. Integrin can directly mediate adhesive bonding of tumor cells and matrix proteins and involves in controlling cytoskeleton and cell proliferation in cells.

According to present researches (as shown in Annotations 1-3), the binding affinity of RGD cyclic peptide multimer with the target is increased with the increase of the amount of RGD cyclic peptide in even number for imaging tumor (RGD$_8$>RGD$_4$>RGD$_2$). However, when the amount of RGD cyclic peptide is too large, it causes problem in imaging. The problem mainly includes having a lower target-background-ratio (TBR) due to the intake of non-target tissues (background), such that the quality of imaging is deteriorated. Thus, the RGD medicine with low affinity and high background intake cannot be practically used for clinical applications. Therefore, it is important to develop a RGD medicine having higher tumor intake and lower background intake.

1. $^{64}$Cu-labeled tetrameric and octameric RGD peptides for small-animal PET of tumor $\alpha_v\beta_3$ integrin expression. Li Z B, Cai W, Cao Q, Chen K, Wu Z. He L, Chen X. J Nucl Med. 2007 July; 48(7):1162-71.
2. $^{68}$Ga-labeled multimeric RGD peptides for microPET imaging of integrin $\alpha_v\beta_3$ expression. Li Z B, Chen K, Chen X. Eur J Nucl Med Mol Imaging. 2008 June; 35(6):1100-8.
3. Micro-PET imaging of $\alpha_v\beta_3$-integrin expression with $^{18}$F-labeled dimeric RGD peptide. Chen X, Tohrne M, Park R, Hou Y, Bading J R, Conti P S. Mol Imaging. 2004 April; 3(2):96-104.

According to the present researches, $^{99m}$Tc-labeled RGD cyclic peptide ($^{99m}$Tc-3P-RGD$_2$) and $^{99m}$Tc-labeled RGD galactose dimer ($^{99m}$Tc-Galacto-RGD$_2$) imaging agent are proved to have great affinity with the expression of integrin $\alpha_v\beta_3$ in malignant tumor (as shown in Annotations 4-5), and they can be imaged by SPECT or SPECT/CT, which can be served as economical agents for tumor diagnosis. However, these two agents are found to still have a relatively high radioactive level of background in abdomen organs in animal bodies, such that the performance of imaging is affected, and the applicability value in abdomen tumor diagnosis is limited.

4. Integrin $\alpha v\beta 3$-targeted radiotracer (99m)Tc-3P-RGD$_2$, useful for noninvasive monitoring of breast tumor response to antiangiogenic linifanib therapy but not anti-integrin $\alpha(v)\beta_3$ RGD$_2$ therapy. Ji S, Zheng Y, Shao G, Zhou Y, Liu S. Theranostics. 2013; 3(11):816-30.

5. (99m)Tc-Galacto-RGD$_2$: a novel 99mTc-labeled cyclic RGD peptide dimer useful for tumor imaging. Ji S, Czerwinski A, Zhou Y. Shao G, Valenzuela F, Sowinski P. Chauhan S, Pennington M, Liu S. Mol Pharm. 2013; 10(9):3304-14.

SUMMARY OF THE INVENTION

According to the disclosure, a SPECT radionuclide-labeled trimeric cyclic RGD peptide is disclosed. The SPECT radionuclide-labeled trimeric cyclic RGD peptide comprises a SPECT radionuclide and a trimeric cyclic peptide (4P-RGD$_3$) having 4 PEGs and three cyclic RGD, combined with the SPECT radionuclide.

According to the disclosure, a method for preparing a SPECT radionuclide-labeled trimeric cyclic RGD peptide is disclosed. The method comprises the following steps. (a) Process for preparing a labeled precursor HYNIC-4P-RGD$_3$is performed, the process comprises the following steps. HYNIC-OSu and 4P-RGD$_3$ is dissolved in DMF with a mole ratio of 8:1 to 12:1. An excess amount of DIEA is incorporated. The mixture is mixed for completing the reaction. DI water is incorporated. Pure TEA is incorporated such that the pH value being within the range of 3-4. The product is purified by HPLC. The collected liquid freeze-dryed. (b) Process for preparing the SPECT radionuclide-labeled trimeric cyclic RGD peptide is performed, the process comprises the following steps. The HYNIC-4P-RGD$_3$ obtained in process (a) is mixed with TPPTS, glycine, mannitol, disodium succinate hexahydrate and succinate acid solution in a mass ratio of 20-25:5000:6500:40000:38500:12700 with Na$^{99m}$TcO$_4$ solution. The mixture is heated. It is standed under room temperature.

According to the disclosure, a method for imaging a tumor by a SPECT radionuclide-labeled trimeric cyclic RGD peptide is disclosed. The method comprises the following steps. The SPECT radionuclide-labeled trimeric cyclic RGD peptide is imaged by a SPECT or a SPECT/CT at the position of the tumor for tracing the position and the activity of the tumor.

BRIEF DESCRIPTION OF THE DRAWINGS

In order to more clearly illustrate the embodiments of the disclosure, the accompanying drawings for illustrating the technical solutions and the technical solutions of the disclosure are briefly described as below.

DETAILED DESCRIPTION OF THE PREFERRED EMBODIMENT

The following description with reference to the accompanying drawings is provided to clearly and completely explain the exemplary embodiments of the disclosure. It is apparent that the following embodiments are merely some embodiments of the disclosure rather than all embodiments of the disclosure. According to the embodiments in the disclosure, all the other embodiments attainable by those skilled in the art without creative endeavor belong to the protection scope of the disclosure.

Figure 1:
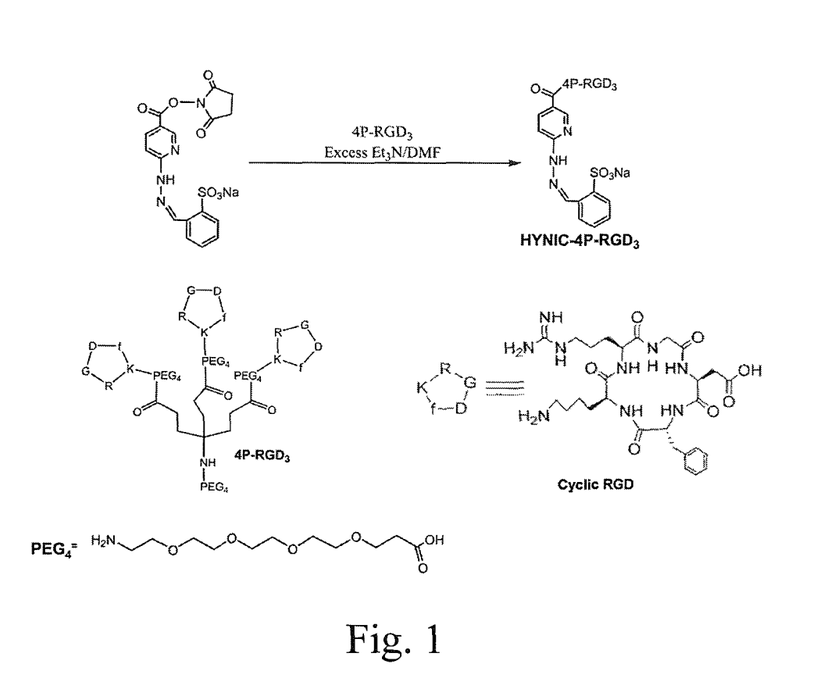
FIG. 1 is a synthetic route and a chemical structure of the labeled precursor, HYNIC-4P-RGD$_3$, as well as the chemical structures of 4P-RGD$_3$, PEG$_4$ and cyclic RGD in the compound according to the embodiments of the disclosure.

Preparation of SPECT radionuclide-labeled trimeric cyclic RGD peptide:

1. Materials and instruments: all the purified chemicals are obtained from Sigma/Aldrich in the U.S. (St. Louis, Mo.). Trimeric cyclic peptide having four polyethylene glycol and three cyclic RGD (4P-RGD$_3$, the chemical structure is shown in FIG. 1) is obtained from Peptides International, Inc in the US (Louisville, Ky.) (as shown in Annotation 6). HYNIC-OSu (Succinimidyl 6-hydrazinonicotinate) is prepared based on the procedure cited in the reference (as shown in Annotation 7).

6. Peptides International, Inc; website: https://www.pep-net.com/

7. Harris, T. D.; Sworin, M.; Williams, N.; Rajopadhye, M.; Damphousse, P. R.; Glowacka, D.; Poirier, M. J.; Yu, K. Synthesis of stable hydrazones of a hydrazinonicatinyl-modifiedpeptide for the preparation of 99mTc-labeled radiopharmaceuticals. Bioconjugate Chem. 1998, 10, 808-814.

MALDI (matrix-assisted laser desorption ionization) spectrum is obtained by Applied Biosystems Voyager DE PRO Mass Spectrometer (Framingham, Mass.). Na$^{99m}$TcO$_4$ is obtained from Lantheus Medical imaging or Global Medical Solutions.

II. HPLC (High Performance Liquid Chromatography) purification:

1. Method 1: the instrument used for purification of semi-preparative HPLC is a LabAlliance HPLC system and a Zorbax C18 semi-preparative column (9.4 nm×250 mm, pore size: 100 Å, Agilent Technologies, Santa Clara, Calif.) including an UV detector (wavelength=254 nm). The gradient elution conditions are: flow velocity: 2.5 mL/minute, the initial mobile phase is 90% of solution A (0.1% TFA aqueous solution) and 10% of solution B (0.1% TFA acetonitrile solution), the mobile phase is linearly changed to 80% of solution A and 20% of solution B after 5 minutes, as well as the mobile phase is linearly Changed to 50% of solution A and 50% of solution B after 20 minutes.

2. Method 2: LabAlliance HPLC system is used for the purification of radio-HPLC, which includes a Ram IN/USdetector (Tampa, FL) and 1 Zorbax C18 column (4.6 mm×250 mm, pore size: 300, Agilent Technologies, Santa Clara, Calif.). The gradient elution conditions are: flow velocity: 1 mL/minute, the mobile phase is 90% of solution A (25 mM ammonium acetate solution) and 10% of solution B (acetonitrile solution) between 0-5 minute, and solution B in the gradient mobile phase is linearly elevated to 60% between 5-20 minutes.

III. Preparation of labeled precursor HYNIC-4P-RGD$_3$:

13.5 mg HYNIC-OSu (30.0 μmol) and 9.0 mg 4P-RGD$_3$ (3.0 μmol) are dissolved in 2.0 mL of dimethylformatnide (DMF). An excess amount of diisopropylethylamine (DIEA) (5 drops) is dropped into the solution, and the mixture is stirred under room temperature until the reaction is completed (about 24 hrs). 2.0 mL of water is incorporated into the mixture, and the pH is adjusted to 3-4 by incorporating pure TFA. The product is purified by HPLC (HPLC method 1), and the composition at 18 minute is collected. After freeze-drying the collected liquid, is 6.5 mg of white powder of HYNIC-4P-RGD$_3$ is obtained as the target product (about 50%). The chemical structure is shown in FIG. 1, and MALDI-MS: m/z MW of $[C_{148}H_{227}N_{35}O_{48}S]=3295.8240$.

Figure 2:
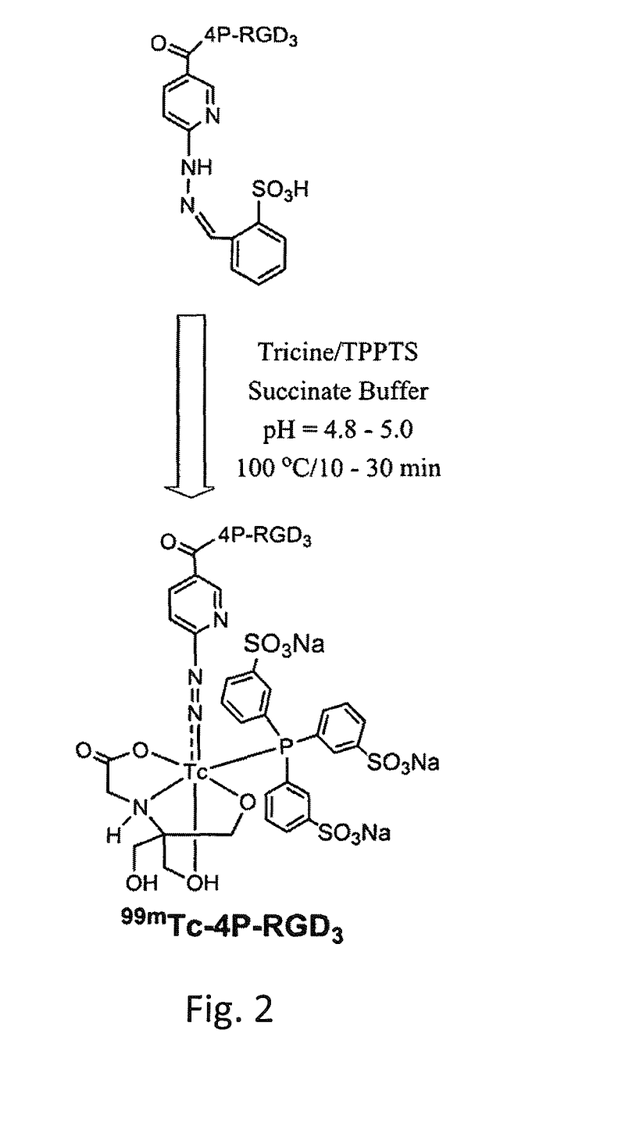
FIG. 2 is a synthetic route and a chemical structure of $^{99m}$Tc labeled tumor imaging tracer, $^{99m}$Tc-4P-RGD$_3$, according to the embodiments of the disclosure.
Figure 3:
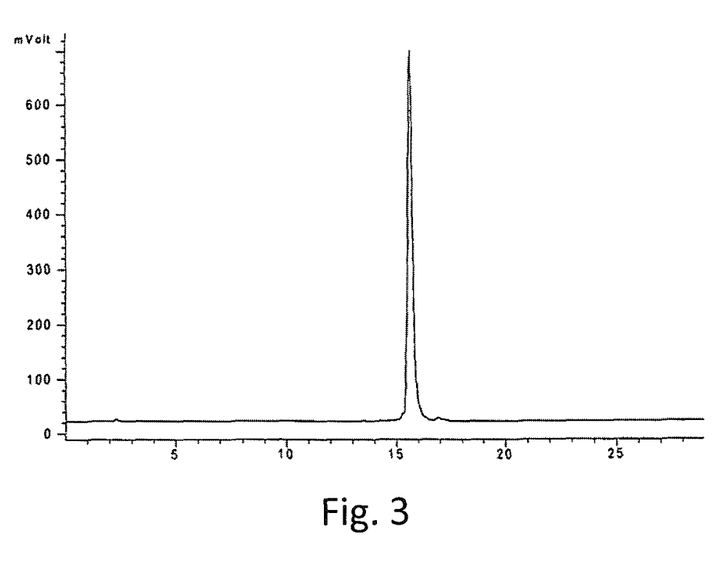
FIG. 3 is radio HPLC spectrum of $^{99m}$Tc-4P-RGD$_3$ according to the embodiments of the disclosure.

IV. Preparation of $^{99m}$Tc-4P-RGD$_3$:

5 mg of TPPTS, 6.5 mg of glycine, 40 mg of mannitol, 38.5 mg of disodium succinate hexahydrate, 12.7 mg of succinate acid solution and 1.0-1.5 mL of Na$^{99m}$TcO$_4$ solution (a physiological saline with the activity of f1110-1850 MBq) are injected into the lyophilized vial containing 20-25 μg of HYNIC-4P-RGD$_3$. The above vial is heated in boiling water bath for 10-20 minutes and then is standed for 5 minutes under room temperature, and a sample solution of $^{99m}$Tc-4P-RGD$_3$ is obtained (the chemical structure is shown in FIG. 2). The radiochemical purity is analyzed by radio-HPLC (HPLE method 2). According to the radio HPLC spectrum of $^{99m}$Tc-4P-RGD-$_3$ (FIG. 3), it can be realized that $^{99m}$Tc-4P-RGD$_3$ has high purity of radiochemical purity (the purity is greater than 90%), such that it can be used in the research of biodistribution and tumor imaging.

V. Biodistribution and preparation of $^{99m}$Tc-4P-RGD$_3$ for tumor imaging:

The preparation of $^{99m}$Tc-4P-RGD$_3$ for the research of biodistribution includes incorporating $^{99m}$Tc-4P-RGD$_3$ solution into physiological saline until the activity concentration is 10-30 mCi/mL. The preparation of $^{99m}$Tc-4P-RGD$_3$ for tumor imaging includes incorporating $^{99m}$Tc-4P-RGD$_3$ solution into physiological saline until the activity concentration is about 10 mCi/mL. During the experiments, each of the animal is injected with about 0.1 mL of the solution.

VI. Animal model:

Biodistribution and tumor imaging are performed under the guidance of US National Institutes of Health animal experiments (1985, NIH 86-23, Laboratory Animal Care). U87MG cells are purchased from US ATCC (Manassas, Va.). Cell culture conditions: DMEM medium (non-essential amino acids sodium pyruvate) containing 10% of fetal bovine serum and 1% of penicillin and streptomycin. The cells are cultured under 37° C. with 5% of $CO_2$. When the cells are grown to 90% confluence, they grow exponentially. The cells can be grown to a single layer, multiple layers or split layers. Female athymic nu/nu nude mice aged 4-5 weeks are used for the experiments, $5×10^6$ of tumor cells are incorporated into 0.1 mL of physiological saline and are planted to shoulder subcutaneous of the mice under sterile conditions. About 4 weeks after planting, the tumor cells grow to 0.1-0.5 g for the use of biodistribution and imaging.

VII. Biodisribution:

7 random U87MG glioma nude mice (20-25 g) are selected. Each of the nude mice is injected at the tail vein with 3 μCi of $^{99m}$Tc-4P-RGD$_3$. After 60 minutes, a great amount of sodium pentobarbital is injected for executing the mice. Blood samples are collected from the mouse hearts. Tumor, normal organs (brain, eyes, heart, spleen, lung, liver, kidney, muscle and intestine) and tumor tissues are collected and washed by saline. Then they are dried by absorbent tissue, weighed by Perkin Elmer Wizard 1480 γ counter (Shelton, Conn.). The organ intake is measured by the percentage of the injection dose per gram of the tissue (% ID/g). The following table compares the biodistribution in U87MG glioma nude mice 60 minutes after the injection between $^{99m}$Tc-4P-RGD$_3$ and currently used medicine, $^{99m}$Tc-Galacto-RGD$_2$ and $^{99m}$Tc-3P-RGD$_2$.

|  | Radioactive Tracer | | |
| --- | --- | --- | --- |
|  | $^{99m}$Tc-Galacto-RGD$_2$ (n = 8) | $^{99m}$Tc-3P-RGD$_2$ (n = 6) | $^{99m}$Tc-4P-RGD$_3$ (n = 7) |
| Blood | 0.56 ± 0.25 | 0.47 ± 0.06 | 0.53 ± 0.14 |
| Brain | 0.35 ± 0.28 | 0.17 ± 0.03 | 0.14 ± 0.01 |
| Eye | 0.81 ± 0.39 | 1.40 ± 0.13 | 0.46 ± 0.23 |
| Heart | 1.27 ± 0.61 | 1.67 ± 0.15 | 0.56 ± 0.19 |
| Small Intestine | 5.45 ± 1.47 | 9.45 ± 1.31 | 1.65 ± 0.37 |
| Kidney | 11.70 ± 4.06 | 12.28 ± 1.09 | 9.10 ± 2.31 |
| Liver | 3.07 ± 2.14 | 2.92 ± 0.77 | 1.92 ± 0.62 |
| Lung | 2.93 ± 0.94 | 4.25 ± 0.63 | 1.14 ± 0.41 |
| Muscle | 0.88 ± 0.34 | 1.12 ± 0.15 | 0.35 ± 0.17 |
| Spleen | 1.99 ± 0.71 | 3.11 ± 0.18 | 1.33 ± 0.52 |
| Tumor | 6.86 ± 1.33 | 7.24 ± 0.95 | 7.34 ± 1.66 |

Figure 4:
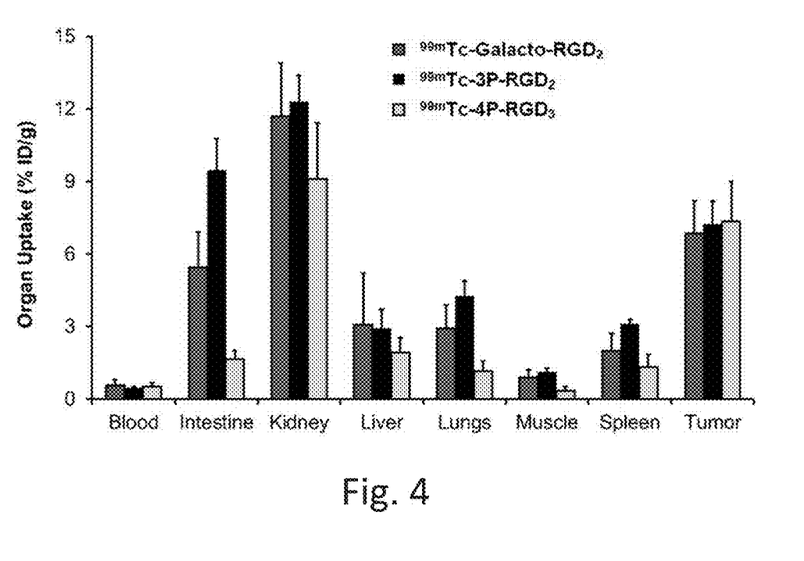
FIG. 4 is the comparison of animal hiodistributions in organs after 60 minutes between $^{99m}$Tc-4P-RGD$_3$ (n=7), $^{99m}$Tc-3P-RGD$_2$ (n=6) and $^{99m}$Tc-galactose-RGD$_2$ (n=8) according to the embodiments of the disclosure.

VIII. FIG. 4 is the comparison of animal biodistributions in organs after 60 minutes between $^{99m}$Tc-4P-RGD$_3$ (n=7), $^{99m}$Tc-3P-RGD$_2$ (n=6) and $^{99m}$Tc-galactose-RGD$_2$ (n=8) according to the embodiments of the disclosure. 60 minutes after the injection, the tumor intake of $^{99m}$Tc-4P-RGD$_3$ (7.34±1.66% ID/g) is highly similar to $^{99m}$Tc-3P-RGD$_2$ (7.24±0.95% ID/g) and $^{99m}$Tc-Galacto-RGD$_2$ (6.86±1.33% ID/g). However, the intake background in organs of the whole body, such as intestine, liver, lung, muscle, spleen and kidney, is significantly decreased. Thus, it can be realized that $^{99m}$Tc-4P-RGD$_3$ can provide a better quality of tumor imaging for whole body as compared to $^{99m}$Tc-3P-RGD$_2$ and $^{99m}$Tc-Galacto-RGD$_2$, and $^{99m}$Tc-4P-RGD$_3$ is more superior for the application of diagnosis of tumors in whole body.

Figure 5:
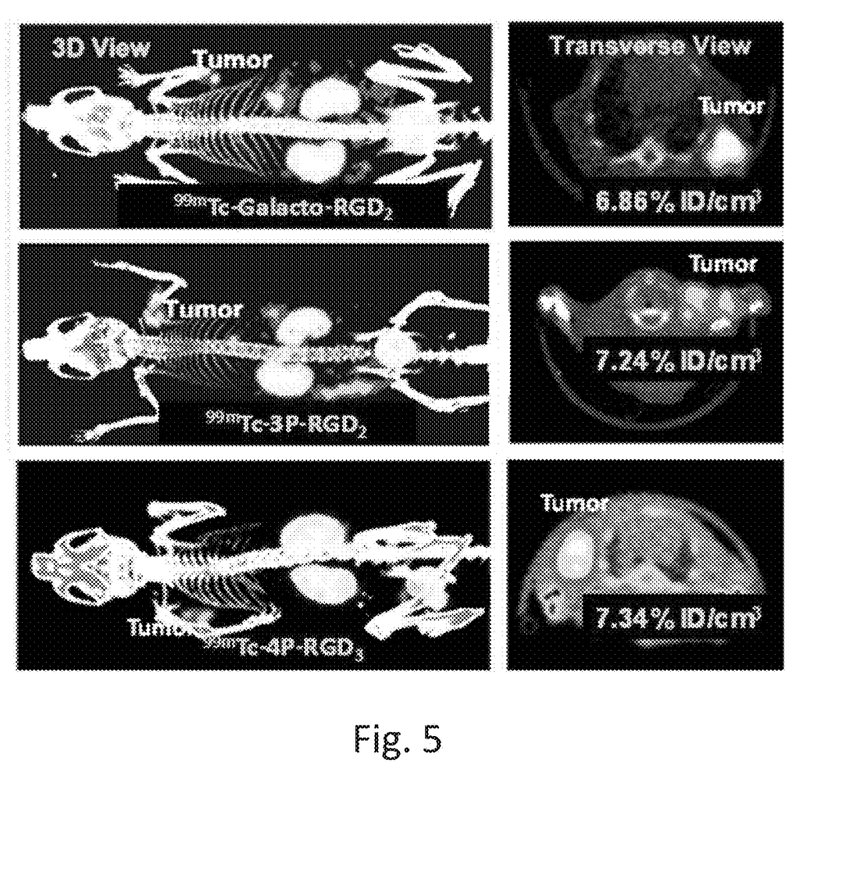
FIG. 5 is a 3D and sectional view of SPECT/CT image of U87MG glioma nude mice after injection of $^{99m}$Tc-galactose-RGD$_2$, $^{99m}$Tc-3P-RGD$_2$ and $^{99m}$Tc-4P-RGD$_3$ (about 37 MBq).

IX. FIG. 5 is a 3D and sectional view of SPECT/CT image of U87MG glioma nude mice after injection of $^{99m}$Tc-galactose-RGD$_2$, $^{99m}$Tc-3P-RGD$_2$ and $^{99m}$Tc-4P-RGD$_3$ (about 37 MBq). The radioactive accumulation in animal abdomen is the lowest after the injection of $^{99m}$Tc-4P-RGD$_3$ (especially in intestines), and the tumor intake is about 7.34 ID/g based on the SPECT quantization. The contrast ratio of the tumor and the background in the SPECT/CT image is great, such that the tumor can be clearly noticed. As compared with the images of $^{99m}$Tc-3P-RGD$_2$ and $^{99m}$Tc-Galacto-RGD$_2$, it can be realized that the image of $^{99m}$Tc-4P-R.GD$_3$ does not have significant background intake of the tissues or organs. According to the SPECT/CT images, it can be clearly realized that is an excellent radioactive tumor imaging tracer for whole body.

X. Normal mice (n=2) are selected for the metabolism research of the stability of $^{99m}$Tc-4P-RGD$_3$ in vivo, Each animal is injected with about 10 MBq of $^{99m}$Tc-4P-RGD$_3$. The bladders are squeezed manually after 30 minutes and 120 minutes, respectively. The urine samples are collected and are mixed with 50% aqueous acetonitrile with the same volume. The mixture is centrifilged under 8,000 rpm. The supernatant is collected and is filtered by a 0.20 μm Millex-LG filter. The filtrate is analyzed by the HPLC. The fecal samples 120 minutes after the injection is collected, and is treated for homogenization by 20% of aqueous acetonitrile. The obtained mixture is rotated for about 5 minutes and then is centrifuged under 8,000 rpm. The supernatant is collected and is filtered by a 0.20 μm. Millex-LG filter. The filtrate is analyzed by the HPLC. The radioactive recovery is greater than 95% for the urine samples and the fecal samples (counted by γ).

Figure 6:
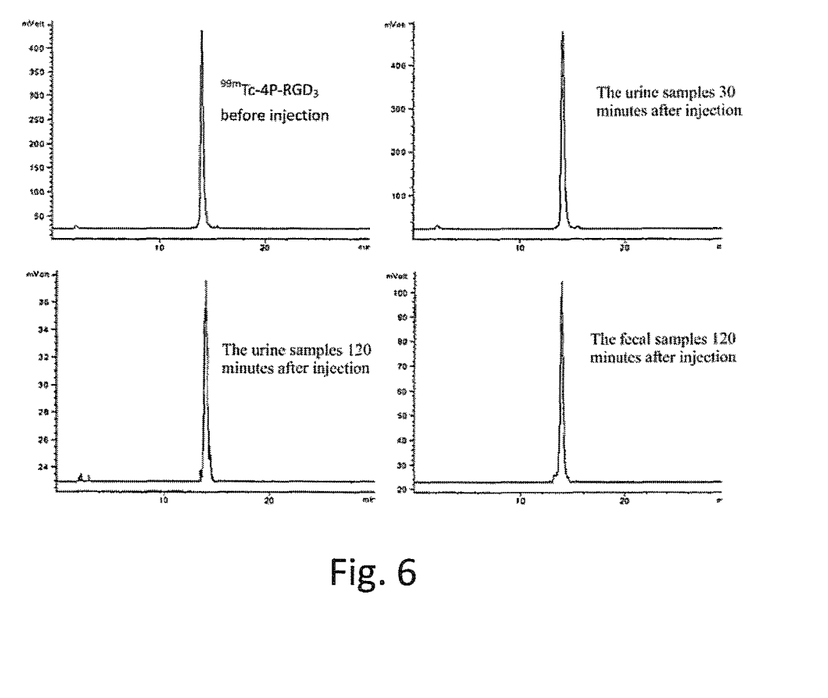
FIG. 6 indicates radioactive HPLC spectrums of the physiological saline before the injection of $^{99m}$Tc-4P-RGD$_3$, urine samples 30 minutes after the injection as well as urine samples and fecal samples 120 minutes after the injection.

XI. FIG. 6 indicates typical metabolisms of $^{99m}$Tc-4P-RGD$_3$, and FIG. 6 indicates radioactive HPLC spectrums of the physiological saline (A) before the injection of $^{99m}$Tc-4P-RGD$_3$, urine samples (B) 30 minutes after the injection as well as urine samples (C) and fecal samples (D) 120 minutes after the injection. According to the spectrums, during the research period, which is over 2 hours, no metabolites of $^{99m}$Tc-4P-RGD$_3$ are detected in the urine samples and the fecal samples. Thus, it indicates that $^{99m}$Tc-4P-RGD$_3$ can be excreted outside animals' bodies in the original form of $^{99m}$Tc-4P-RGD$_3$ after metabolism.

Note that the specifications relating to the above embodiments should be construed as exemplary rather than as limitative of the present disclosure. The equivalent variations and modifications on the structures or the process by reference to the specification and the drawings of the disclosure, or application to the other relevant technology fields directly or indirectly should be construed similarly as falling within the protection scope of the disclosure.

What is claimed is:

1. A method for preparing a SPECT radionuclide-labeled trimeric cyclic RGD peptide comprising: a SPECT radionuclide; and a trimeric cyclic peptide (4P-RGD$_3$) having four PEG and three cyclic RGD, combined with the SPECT radionuclide, wherein the SPECT radionuclide is $^{99m}$Tc and the chemical structure of SPECT radionuclide-labeled trimeric cyclic RGD peptide is $^{99m}$Tc-4P-RGD$_3$, comprising:
   (a) process for preparing a labeled precursor HYNIC-4P-RGD$_3$, comprising:
      dissolving HYNIC-OSu and 4P-RGD$_3$ in DMF with a mole ratio of 8:1 to 12:1;
      adding 5 drops of DIEA to form a mixture;
      mixing the mixture to complete reaction of HYNIC-OSu and 4P-RGD$_3$ to form HYNIC-4P-RGD$_3$;
      adding deionized water to the HYNIC-4P-RGD$_3$;
      adding pure trifluoroacetic acid to adjust pH range within-3-4;
      purifying the HYNIC-4P-RGD$_3$ by HPLC to obtain a collected liquid; and
      freeze-drying the collected liquid;
   (b) a process for preparing the SPECT radionuclide-labeled trimeric cyclic RGD peptide, comprising:
      mixing the HYNIC-4P-RGD$_3$ obtained in process (a) with triphenylphosphine trisulfonate, glycine, mannitol, disodium succinate hexahydrate and succinate acid solution in a mass ratio of 20-25:5000:6500:40000:38500:12700 with Na$^{99m}$TcO$_4$ solution to form a mixture $^{99m}$Tc-4P-RGD$_3$;
      heating the mixture; and
      keeping the mixture below room temperature.

2. The method according to claim 1, wherein in (a), HYNIC-OSu and 4P-RGD3 are dissolved in DMF with a mole ratio of 10:1.

3. The method according to claim 1, wherein in (a), the mixture is mixed for 24 hrs to complete the reaction of HYNIC-OSu and 4P-RGD$_3$.

4. The method according to claim 1, wherein in (b), the mixture is heated in boiling water bath for 10-20 minutes.

5. The method according to claim 1, wherein in (b), the mixture is kept below room temperature for5minutes.

* * * * *